(12) United States Patent
Ostermeyer et al.

(10) Patent No.: US 9,448,161 B2
(45) Date of Patent: Sep. 20, 2016

(54) OPTICAL DEVICE, PARTICULARLY A POLARIMETER, FOR DETECTING INHOMOGENEITIES IN A SAMPLE

(75) Inventors: Martin Ostermeyer, Gehrden (DE); Gerhard Pfeifer, Gratkorn (AT)

(73) Assignee: Anton Paar GmbH, Graz (AT)

(*) Notice: Subject to any disclaimer, the term of this patent is extended or adjusted under 35 U.S.C. 154(b) by 827 days.

(21) Appl. No.: 13/565,299

(22) Filed: Aug. 2, 2012

(65) Prior Publication Data
US 2013/0258336 A1    Oct. 3, 2013

(30) Foreign Application Priority Data

Mar. 30, 2012 (DE) .................. 10 2012 205 311

(51) Int. Cl.
| | | |
|---|---|---|
| *G01N 21/21* | (2006.01) | |
| *G01J 4/04* | (2006.01) | |
| *G01N 21/94* | (2006.01) | |
| *G01N 21/88* | (2006.01) | |
| *G01N 21/90* | (2006.01) | |
| *G01N 21/59* | (2006.01) | |
| *G01J 4/00* | (2006.01) | |
| *G01N 21/29* | (2006.01) | |

(52) U.S. Cl.
CPC ............... *G01N 21/21* (2013.01); *G01J 4/04* (2013.01); *G01N 21/211* (2013.01); *G01N 21/59* (2013.01); *G01N 21/8803* (2013.01); *G01N 21/8806* (2013.01); *G01N 21/90* (2013.01); *G01N 21/9027* (2013.01); *G01N 21/94* (2013.01); *G01J 2004/001* (2013.01); *G01N 21/29* (2013.01); *G01N 2021/8848* (2013.01)

(58) Field of Classification Search
None
See application file for complete search history.

(56) References Cited

U.S. PATENT DOCUMENTS

| | | | | | |
|---|---|---|---|---|---|
| 1,959,785 | A | * | 5/1934 | Gray ...................... | G01N 21/21 356/33 |
| 2,503,808 | A | * | 4/1950 | Earl ........................ | G01J 4/04 250/204 |
| 4,355,231 | A | * | 10/1982 | Lauer ..................... | G01V 9/005 250/253 |
| 5,013,153 | A | * | 5/1991 | Disch ...................... | G01J 3/12 356/453 |
| 5,786,894 | A | * | 7/1998 | Shields et al. ............. | 356/338 |
| 6,311,550 | B1 | * | 11/2001 | Lehmikangas et al. ..... | 73/61.71 |

(Continued)

FOREIGN PATENT DOCUMENTS

| | | |
|---|---|---|
| DE | 100 04 889 B4 | 5/2004 |
| DE | 699 38 274 T2 | 2/2009 |

(Continued)

OTHER PUBLICATIONS

Chipman, R.A., "Polarimetry," Chapter 22 in "Handbook of Optics vol. II," Michael Bass (ed.), Optical Society of America, 1995.
Azzam, R.M.A., "Ellipsometry," Chapter 27 in "Handbook of Optics vol. II," Michael Bass (ed.), Optical Society of America, 1995.
SIPO Office Action, dispatched Apr. 5, 2016 in application 20131009961.8, which is a Chinese language family member of the above-referenced application.

*Primary Examiner* — Gordon J Stock, Jr.
(74) *Attorney, Agent, or Firm* — Robert A. Blaha; Smith Tempel Blaha LLC

(57) ABSTRACT

An optical device, particularly a polarimeter, is provided for analyzing a liquid sample, having: a light-generating system for generating light for the surface irradiation of the sample; a detection system which is set up for the spatially resolved detection of light which originates from the transmission of the light provided for the surface irradiation through the sample; a telecentric optical system with a lens between the sample and the detection system and with an aperture diaphragm in the focal plane of the lens between the lens and the detection system.

19 Claims, 3 Drawing Sheets

(56) References Cited

U.S. PATENT DOCUMENTS

| | | |
|---|---|---|
| 6,643,021 B1 | 11/2003 | Kawamura |
| 2003/0174323 A1* | 9/2003 | Wagner .................. G01N 21/21 356/246 |
| 2005/0094144 A1* | 5/2005 | Gibbs .................... G01N 21/21 356/365 |
| 2007/0165210 A1 | 7/2007 | Wang et al. |
| 2008/0231854 A1* | 9/2008 | Seifert et al. ................. 356/335 |
| 2011/0229840 A1 | 9/2011 | Liang et al. |
| 2013/0201471 A1* | 8/2013 | Bui et al. ........................ 356/73 |

FOREIGN PATENT DOCUMENTS

| | | |
|---|---|---|
| DE | 10 2008 001 291 B3 | 7/2009 |
| SU | 1749783 A1 * | 7/1992 |

* cited by examiner

OPTICAL DEVICE, PARTICULARLY A POLARIMETER, FOR DETECTING INHOMOGENEITIES IN A SAMPLE

TECHNICAL FIELD

The present invention relates to an optical device, particularly a polarimeter, for analyzing a liquid sample, the optical device being constructed to detect inhomogeneities in the liquid sample. Further, the optical device is preferably constructed to measure isotropic polarization properties of the liquid sample.

BACKGROUND

In a conventional polarization measurement with the aid of a polarimeter, a measuring beam of defined wavelength and a defined polarization state is generated with the aid of a light source and with a polarizer and the sample to be investigated is irradiated with this polarized measuring beam. If an optically active substance, for example in dissolved form, is located in the sample, then the polarization state of the measuring beam changes during the irradiation of the sample. The polarization state of the measuring beam radiated through the sample is rotated in particular with regards to a polarization direction and is checked or determined by means of an evaluation unit. In this case, an analyzer is arranged within a beam path which likewise changes the polarization state of the measuring beam or only allows a certain polarization state to pass.

Either the orientation of the polarizer, the orientation of the analyzer or the orientations of both the polarizer and the analyzer is/are changed in order to minimize an intensity of measuring radiation received at a detector. From the orientations or rotations of the polarizer and/or of the analyzer, the change of the polarization state due to the irradiation through the sample can be deduced. In particular, the rotation of the polarization direction due to the irradiation through the sample can be determined. In turn, a concentration of optically active substances in the sample can, for example, be determined from the rotation value.

When carrying out a polarization measurement by using a conventional polarimeter, the measurement can be distorted, in particular by inhomogeneities of the sample, which can make the determination of the isotropic polarization properties of the sample difficult or impossible.

The following phenomena can inter alia fall within the concept of inhomogeneity:
1. gas bubbles which were either present before the filling of a sample container, particularly a cuvette, or which arise due to turbulences when filling the cuvette
2. particles made up of impurities
3. insufficient mixing of a sample. This can e.g. take place if the sample is prepared, e.g. diluted, prior to the measurement process and is then not mixed or homogenized well enough. A further example are solid samples which are dissolved for measurement and may contain particles of non-dissolved substance.
4. displaced residues of earlier samples.

Inhomogeneities constitute a significant practical problem. The known methods for avoiding inhomogeneities are not reliable enough or are too complex or have another negative side effect, so that as before, there is a risk of false measurements due to inhomogeneous samples.

As inhomogeneities therefore cannot be reliably prevented, the need of being able to detect the same still exists. After the detection of inhomogeneities, countermeasures can then be taken, or at least false measurement values can be discarded. In order to be available to fulfill the, particularly in the pharmaceutical field, high quality requirements, the detection of inhomogeneities must be very reliable.

A known method for detecting inhomogeneities consists in directly visually examining the filled cuvette and after that to evaluate the same. However, carrying out this method is in many cases not possible, e.g. because the cuvette body consists of a non-transparent material or because the cuvette is inserted in the measuring device in such a manner that a direct look into the liquid is blocked.

Thus, in practice, the cuvette is often removed from the measuring device before each measurement, in order to be able to see directly through the cuvette. Although this procedure is informative, it is so impractical and time-consuming that it is very often omitted in practice. In addition, it prevents an automation e.g. by means of through-flow cuvettes, funnel cuvettes or autosamplers.

Furthermore, when carrying out these known methods, no objectively verifiable result can be documented, rather only the result of the subjective assessment of a user. This is often not sufficient for quality assurance.

U.S. Pat. No. 6,643,021 B1 discloses a checking method of a measuring system for determining an optical property, the optical property of a liquid sample being measured in that first light is projected in order to analyze the transmitted light. The method further comprises projecting additional light in a path of the first light or in a periphery thereof, in order to, based on an intensity of transmitted light of the second light, detect the presence or the absence of bubbles and/or particles which can interfere with the transmission of the first light. Following detection of the bubbles and/or particles, the same can be removed.

This approach can only succeed if it is ensured that all of the samples to be measured—in the case of homogeneous filling of the cuvette—have the same transmission for the second light beam. In an example of the U.S. Pat. No. 6,643,021 B1, the UV absorption of protein samples is e.g. measured with the first light beam in the measuring device. As proteins do not exhibit any absorption in the NIR, in this case, the intensity of the second light beam in the NIR can be used for detecting inhomogeneities.

The fundamental weakness of this known method, however, is the fact that an attenuation of the second light beam due to an absorption of a homogeneous sample is interpreted as an inhomogeneity. Thus, the method always fails when samples with an arbitrary absorption spectrum are to be measured. It is only possible in certain cases to find a suitable wavelength at which the investigated samples reliably do not exhibit any absorption.

A further disadvantage of the method from U.S. Pat. No. 6,643,021 consists in the fact that, even if it leads to a detection of an inhomogeneity, the intensity attenuation does not enable any differentiation of various types of inhomogeneities, such as bubbles or streaks due to sample carryover. This makes the determination of suitable countermeasures difficult. Sample carryovers or dirt particles can e.g. not be removed with the measures recommended in the patent for eliminating bubbles—such as shaking or ultrasound—rather the same can only be overcome by means of refilling the cuvette.

There is therefore a need for a device and a method for detecting inhomogeneities, in which the cuvette can remain in the measuring device in a position ready for measuring and which allow satisfactory documentation for a modern quality assurance.

SUMMARY

In particular, a requirement for an optical device for analyzing a liquid sample may exist, by which inhomogeneities of the liquid sample can be detected and wherein the optical device is in particular designed in particular for measuring polarization-changing properties of the sample.

It is an object of the present invention to provide an optical device, particularly a polarimeter, which is constructed for detecting inhomogeneities of the sample without having to remove the sample from the measuring device for an analysis of this type.

According to one embodiment of the present invention, an optical device, particularly a polarimeter, is provided for analyzing a liquid sample, the optical device having a light-generating system (having one or a plurality of light sources) for generating light for surface irradiation of the sample (particularly over a cross-sectional area of the sample contained in a sample container, particularly a cuvette), a detection system which is configured for spatially resolved detection of light which originates from the transmission of the surface irradiation through the sample, and a telecentric optical system with a lens arranged between the sample and the detection system and an aperture diaphragm (the aperture window of which can in particular be set with regards to the size and/or shape) in the focal plane of the lens between the lens and the detection system.

The light-generating system only needs to have one (single) light source and the detection system only needs to have one (single) surface detector. The optical device can in particular be designed as a polarimeter.

In order to be able to assess the homogeneity of the sample on the basis of the two-dimensional image of the spatially resolved detector, it is advantageous if the surface illumination, i.e. the light provided for the surface irradiation, has an intensity distribution which is as laterally homogeneous as possible. This can in particular be achieved by choosing an inherently homogeneous light source, here mention may in particular be made of LEDs with phosphorus conversion and also gas discharge lamps. Should the light source not inherently radiate homogeneously enough, then a homogenization (to obtain a laterally homogeneous intensity distribution) can be achieved by means of additional elements (homogenizers).

Examples for inhomogeneously radiating light sources are incandescent lamps, in which the structure of the filament can disturb the homogeneity, as well as light-emitting diodes, in which the emitter surface is structured by means of electrodes or bond wires.

The light provided for surface irradiation can comprise identically (or at least approximately identically) directed light beams ("directed light") and/or diffuse light. The diffuse light can comprise a plurality of light beams, the propagation directions of which are different. The diffuse light can for example be generated by means of scattering of directed light at an opaque element, such as a frosted glass plate for example.

The light provided for surface irradiation can be homogeneous over the beam cross section or can be homogenized. One option for achieving a directed homogeneous illumination is a use of a diffuser and subsequent collimation.

Other (more light-intensive but somewhat more expensive) methods are e.g.

guiding in a sufficiently long multimode glass fiber. Mode mixing ensures homogenization without substantially increasing the numeric aperture.

use of special homogenizing optical waveguides. They have a polygonal cross section, for the most part hexagonal, and manage with a running length of a few centimeters. Also here is the numeric aperture essentially retained.

The liquid sample can be accommodated in a sample container, particularly a cuvette. The cuvette can have an inlet window and an outlet window which allow passage of light of a certain cross-sectional area. The detection system can have one or a plurality of light-sensitive sensors.

The telecentric optical system can be constructed and arranged for imaging a projection of the irradiated sample onto the detection system. The telecentric optical system can in particular be an optical system which is telecentric on the object side. The aperture diaphragm can in this case be arranged in the image-side focal plane of the lens. The lens can in particular comprise a lens system consisting of a plurality of lenses (convex and/or concave) arranged one behind the other. Accordingly, the aperture diaphragm can be arranged in the image-side focal plane of the lens system. In the case of the object-side telecentric optical system, all of the main beams in the object space run parallel to the optical axis. The optical axis can in this case be guided through the inlet window and the outlet window of the cuvette.

The sample is irradiated along a sample irradiation path between the inlet window and the outlet window of the cuvette. The detection system can in particular have an imaging detection unit. The detection system includes a two-dimensional image of the projected sample on the basis of the surface irradiation of the sample and the imaging with the telecentric optical system. Various points along the sample irradiation path are imaged onto an identical point in the image space by means of the telecentric optical system. As a result, a pixel (of the image), which is captured by means of the detection system, contains information of a projection of the sample along the sample irradiation path.

A completely homogeneous sample leads to a completely contrast-free image which is captured by the detection system. If, however, inhomogeneities are present in the sample, such as air bubbles or streaks due to incomplete mixing or incomplete dissolving of components, then an image is captured by the detection system which has contrasts, i.e. different intensities at different pixels, i.e. bright regions and dark regions, in accordance with the inhomogeneities. The projection along the sample irradiation path is achieved by means of the telecentric optical system, which leads in particular to a constant imaging scale for different object points along the sample irradiation path.

The opening size of the aperture diaphragm can be set in dependency of the requirements for a constancy of the imaging scale and in particular in dependency of requirements for image sharpness. In particular, the aperture diaphragm can provide a circular light-transmission region.

The sample container or the cuvette can be irradiated over an overall cross section (of the inlet window and/or of the outlet window) (or between 50% and 100%, particularly 60% and 80% of the overall cross section) with a light beam in the direction of the optical axis. The image of the irradiated sample can be recorded by means of an imaging detector.

Cuvettes with up to 200 mm length (or between 50 mm and 200 mm) can be used.

With conventional imaging systems, for a satisfactory resolution, the focal plane must be moved along the optical axis by refocusing, because it is not possible to achieve a sufficiently large depth of focus over the overall irradiation length of the cuvette. Disadvantageous about such a conventional solution is on the one hand the outlay for the tracking, but it is more serious that the homogeneity can only be assessed by using a series of images of different focal planes or by a continuous film.

Against this background, it is surprising that with the aid of a telecentric imaging, one may succeed in achieving a sufficiently sharp resolution over the entire length of the cuvette, so that the homogeneity in the entire measurement volume can be assessed and documented with a single image.

In this regard, the telecentric imaging fulfils at least three objects:
1. An object-side telecentry ensures that the cross section of the cuvette is imaged onto the detector over the entire length with substantially the same imaging scale.
2. The small aperture of the system realized by means of the small telecentric aperture creates a very deep depth of focus so that the system can image inhomogeneities at any desired position within the cuvette with practice-relevant resolution without any refocusing.
3. In typical polarimeters, the beam path is strongly collimated by the cuvette. The combination of quasi-parallel illumination and telecentric detection is particularly suitable in order to make streaks visible with a high contrast. Thus, inhomogeneities of the above types 3 and 4 (defective mixing and sample carryover) can be detected particularly well. Telecentric detection is here clearly superior to both visual checking and detection systems with normal imaging.

An object-side telecentric beam path is used to detect objects without perspective distortion. The entrance pupil of the telecentric optical system is located at infinity so that the main beams all run parallel to the optical axis in the interior of the cuvette. The diameter of the lens must therefore be at least as large as the diameter or the linear extent of the in- or outlet window of the cuvette. The imaging scale of an object located in the cuvette (bubble, streak, etc.) does not change over the entire length of the cuvette (in the case of axial displacement along the optical axis or the sample irradiation path). An object-side telecentric beam path can be realized in the simplest manner by means of a single collimating lens with an aperture diaphragm in the object-side focal plane.

In order to achieve an image of sufficient depth of focus, at least one single telecentric imaging is used. The telecentric optical system stands out on account of the fact that the entrance or exit pupil is located at infinity.

According to one embodiment of the present invention, the telecentric optical system has a further lens (or a further lens system) between the aperture diaphragm and at least one part of the detection system, particularly a surface detector, the further lens being arranged in such a manner that the aperture diaphragm is located in the object-side focal plane of the further lens, in order to achieve a double telecentric imaging of a projection of the sample along the optical axis on the surface detector.

By use of the double telecentric imaging, the detection system, particularly the surface detector, can be displaced along the optical axis without changing the imaging of the projection of the sample (particularly with respect to the image size) along the optical axis on the surface detector. As a result, greater flexibility can be provided for the structure of the device. A displacement of the sample relatively to the lens, the aperture diaphragm and the further lens does not lead to any change of the imaging of the projection of the sample along the optical axis on the surface detector.

Thus, an adjustment of the individual components of the optical device can be simplified.

According to one embodiment of the present invention, the light-generating system is further constructed for generating a measuring light beam (which has a plurality of light beams, which propagate at least approximately along an identical direction, particularly along the optical axis), the measuring light beam propagating through the sample along an optical axis. In this case, the optical axis in particular runs through the inlet window and the outlet window of the sample container, particularly the cuvette. In contrast to the in particular homogenized or homogeneous surface illumination, the measuring light beam can have a lateral structure, which is caused e.g. by means of a structure of the emitter. The measuring light beam can in particular have a defined polarization state in this case.

Thus, the optical device can also be constructed as a polarimeter.

The measuring beam generated for polarization measurement can in this case also be used for investigating the filling quality, or an additional light source with fitting properties can be used. To this end, elements such as beam splitters and/or diverting mirrors can be used to carry out the filling quality independently of the polarimeter measurement. In addition to the measuring beam sources, any desired additional radiation sources can also be used. A criterion for these lamps is the visible range of the spectrum and/or spectrum portions beyond the same, which in combination with a suitable detector result in an image for the filling state which can be evaluated.

Any desired surface detectors, e.g. CCD camera chips, intensified CCDs, diode arrays, NMOS, CMOS, can be used as detectors for the detection system. If appropriate, the detector of the polarimeter can also be used in a spatially resolved manner and scan the image in a suitable and spatially resolved manner. The detector can in this case be sensitive over the entire spectral range or else assess the wavelength of the measuring light only over a partial region of the spectrum, or monochromatically, and therefore also become insensitive to extraneous light.

In order to be able to identify any desired inhomogeneities in the cuvette by use of a telecentric optical system, an even illumination of the entire cuvette cross section with the homogenized light should be ensured. If the spatially delimited measuring beam is used directly as an imaging light source, then the same can be expanded to a surface-directed beam bundle e.g. by means of an expansion optical system and/or expanded and homogenized by means of a diffuser (ground glass plate, frosted glass plate, holographic film).

When the filling quality is ensured, the polarimeter measurement is started. To this end, if appropriate, the homogenizer and/or the telecentric optical system are folded out of the measuring beam. Alternatively, the optical paths of the measuring beams for the filling quality testing and polarization determination can be guided separately from one another by means of partially transparent components and/or diverting mirrors in front of and/or behind (upstream and/or downstream of) the cuvette or the sample.

If, in all of these cases, the presence of inhomogeneities is detected by visual assessment of the two-dimensional image by the user or by an automated or semi-automated image recognition, then different procedures can be defined depending on the type of contamination. For example, an attempt can be made to remove bubbles by means of methods known from the prior art (see e.g. the methods disclosed in U.S. Pat. No. 6,643,021 B1). For example, manual or automatic tipping of the cuvette and also ultrasound excitation may be mentioned by way of example here.

In the case of presence of inhomogeneities, such as streaks or displacements, the program flow can provide automated cleaning and/or refilling of the cuvette. In a semi-automated variant, the measurement can be stopped and the user can be informed of the type and size of the contamination by an output on the screen, if appropriate with a documenting image, or the size of the measuring error caused thereby can be indicated. Thus, the user can decide whether the measurement should take place despite the artifact.

The invention relates to polarimeters which measure the isotropic polarization properties of liquid samples. According to one embodiment, a typical polarimeter comprises e.g.
  light source(s)
  means for shaping and guiding the measuring beam
  means for preparing a defined polarization state of the light (polarization state generator, PSG)
  cuvette with the sample for investigation, which is irradiated along the cuvette axis with the measuring beam
  means for analyzing the changes in polarization properties of the measuring beam (polarization state analyzer, PSA) caused by the passage through the sample
  means for spectral selection of the light
  means for determining the sample temperature
  means for detecting the light irradiating the aperture
  evaluation unit with display unit for the determined sample properties.

Generally, the invention can be applied for all polarimeters which investigate the isotropic polarization properties of liquid samples, independently of the precise below-described embodiment of the polarimeter. R. A. Chipman, "Polarimetry", Chapter 22 in "Handbook of Optics Vol II", Michael Bass (ed.), Optical Society of America 1995 gives an overview.

In addition to thermal light sources (incandescent lamps), light-emitting diodes, light-emitting diodes with wavelength conversion, superluminescent diodes, lasers, wide band discharge lamps, narrow band discharge lamps, such as hollow cathode lamps, and low-pressure spectral lamps in particular are suitable as suitable light sources. A plurality of light sources can also be exchanged automatically or manually or can be permanently combined (e.g. by means of wavelength selective elements) to form a measuring beam. The measuring beam can further be prepared with diffusers and/or homogenizers and guided with lenses or mirrors.

Polarization state generator (PSG) and polarization state analyzer (PSA) can be realized in accordance with diverse principles. PSGs and PSAs with fixed, rotating or modulated polarization filters, retarder plates, polarization compensators and beam splitters can be used according to embodiments of the invention. Further embodiments of PSGs, PSAs and also the associated measuring and evaluation technologies are also described in connection with ellipsometers in R. M. A. Azzam, "Ellipsometry", Chapter 27 in "Handbook of Optics Vol II", Michael Bass (ed.), Optical Society of America 1995, but they can however also be used in general polarimeters.

Depending on the embodiment of PSG, PSA and evaluation algorithm, all or single components of the Müller matrix of the sample can be determined as sample property. One example is the optical activity of the sample, which is measured by the rotation of the polarization direction of linearly polarized light caused by the sample.

The polarization properties of samples generally depend on the wavelength of the light, thus a wavelength-selective measurement can be carried out. For example, color filters, interference filters, monochromators or simultaneously multichannel spectrally selective detectors (e.g. array spectrometers) can be used for spectral selection. A spectral fine adjustment can e.g. take place by tipping of interference band pass filters, displacement of graduated interference filters or variation of the emitter temperature of the light source.

The polarization properties of samples generally also depend on the sample temperature, thus the same can be measured by means of temperature sensors dipped into the sample or arranged at the cuvette.

Photomultipliers, photodiodes, avalanche diodes, as well as CCD, NMOS and CMOS detectors can are possible as detectors.

As an example, a polarimeter measures the optical activity of a substance. The property of chemical compounds in the solid state or in solution to rotate the plane of polarized light during passage by a certain amount characteristic for the relevant compound (rotation value) is denoted optical activity.

Optically active substances play a large role in many research fields, but particularly in the research and production of chiral molecules in the chemical and pharmaceutical industry, in the food industry (for example in the characterization of sugar and starch) through to the monitoring and regulation of physical/chemical and biotechnical processes.

To determine the rotation value $\alpha$, the sample to be investigated is placed between two polarization filters (Nicol prisms, Glan-Thompson polarizers, or tourmaline plates or film polarizers). In the 1st filter (polarizer), the parallel incident light is polarized. If the 2nd filter (analyzer) is rotated through 90° with respect to the polarizer, then no light passes through it. If the optically active substance (the liquid sample) is now placed between the filters, then the same rotates the polarization direction of the passing light and one must re-rotate the analyzer or the polarizer through an angle in order to again achieve elimination. This rotation angle is proportional to the rotation property of the substance and the concentration thereof.

A source with polarizer can generate the polarized measuring beam of defined wavelength and irradiate the sample to be investigated along the optical axis. The polarimeter cuvette can contain the sample to be investigated and can be transparent for the measuring radiation at least at the end faces thereof which are perpendicular to the optical axis. The polarization state of the measuring beam rotated by the sample can be checked by use of an evaluation unit, an analyzer, which for the most part is arranged at the outlet of the cuvette, as well as a detector, which at least determines an intensity of the measuring beam, being used. The results can be fed to an evaluation and display unit, and the analysis can for example take place by defined rotation of the analyzer using a motor. The regulation can take place on the basis of the intensity value of the measuring radiation transmitted by the detector, e.g. by means of predetermination of steps for a step motor. In addition, a temperature measurement can also take place for the most part.

The measurement principle can be realized in detail by means of differently structured measuring devices, for example not only the analyzer but also the polarizer can be rotated by use of a motor until the rotation is compensated by use of the investigated substance. To this end, the polarization plane of the measuring beam can be frequency-modulated by use of a Faraday modulator and the measuring signal can be detected at the detector with the same frequency, in order to compensate disruptive influences (scattered light). Measurements of this type can run in the direction of minimal intensity (polarizer and analyzer are intersected).

According to one embodiment of the present invention, the optical device, particularly the polarimeter, has a polarization state generator which is arranged upstream (with respect to a propagation direction of the measuring light beam) of the sample in the optical axis and is set up to, together with the light generating system, generate the measuring light beam with a defined polarization state.

The polarization state can e.g. be a linearly polarized state or a circularly polarized state or an elliptically polarized state of the measuring light beam. The polarizer can e.g. only allow light to pass which is linearly polarized along a certain direction, it being possible to set this direction by rotating the polarizer. Thus, a polarimeter can be constructed in a simple manner.

According to one embodiment of the present invention, the optical device further has a homogenizer arranged in the optical axis, the, in particular homogenized, light provided for surface irradiation being generated by means of passage of the measuring light beam through the homogenizer.

The homogenizer can comprise a diffuser. The diffuser can for example comprise an opaque plate, for example a glass plate, particularly a frosted glass plate. The light of the measuring light beam is converted into a plurality of light beams by the diffuser, which beams have different propagation directions. Thus, diffuse illumination of the sample can be achieved.

Further, an individual or single light source may be sufficient in order to generate both the measuring light beam and light for the homogeneous surface illumination. Thus, the optical device can be simplified.

If the light source used is inherently inhomogeneous, the same can be homogenized by means of diverse methods known in the prior art (for example by means of a homogenizer). In particular, diffusers such as ground glass plates, frosted glass plates, holographic films, structured diffractive elements, microlens arrays, but also optical waveguides, particularly glass fibers and also optical waveguides with polygonal cross section can be used.

According to a further embodiment, inhomogeneities of the imaging light source can be suppressed or subsequently corrected by use of computational methods in the evaluation unit using software. For example, a reference image of a homogeneously filled cuvette can be used to this end: According to this embodiment, devices for homogenizing a light source with inherently unsatisfactory homogeneity for surface illumination can be dispensed with. Instead, the two-dimensional image of the surface detector is homogenized in an evaluation unit using software, for example in that a reference image with a homogeneously filled cuvette (for example for calibration) is called upon. Suitable algorithms can balance the inhomogeneities that are visible in this reference image due to the inhomogeneous illumination with the subsequently recorded images, so that only the inhomogeneities caused by the sample are illustrated. The further detection of sample inhomogeneities is then based on the thus corrected two-dimensional image.

According to one embodiment of the present invention, the homogenizer can be pivoted out of the optical axis and into the optical axis, in order to alternatively either direct the measuring light beam or the, in particular homogenized, light provided for surface irradiation onto the sample.

In this case, according to this embodiment, the measuring light beam and the homogeneous light provided for surface irradiation are not directed onto the sample simultaneously, but rather temporally offset or in succession. Thus, in a simple manner, for detecting the inhomogeneities within the sample, the in particular homogeneous light provided for surface irradiation can be directed onto the sample by pivoting the homogenizer in, and for determining the polarization changing properties of the sample, the homogenizer can be pivoted out of the optical axis in order to thus direct the measuring light beam onto the sample. Thus, the optical device can be structured in a simple and compact manner.

According to one embodiment of the present invention, the light-generating system has a first light source for generating the, in particular homogeneous, light provided for the surface irradiation and a second light source for generating the measuring light beam, the device having an illumination mirror in order to direct the homogeneous light and/or the measuring light beam onto the sample. The in particular homogeneous light provided for surface irradiation and the measuring light beam can in this case be directed simultaneously or temporally successively onto the sample. Provision of a first light source and a second light source in particular enables the use of various wavelength ranges for the homogeneous light and/or the measuring light beam.

According to one embodiment of the present invention, the illumination mirror is transparent to some extent, in particular semi-transparent, in order to simultaneously direct both the in particular homogeneous light provided for surface irradiation and the measuring light beam onto the sample. Here, the illumination mirror can in particular be installed fixedly, i.e. the same cannot be moved or pivoted.

Further, the in particular homogeneous light provided for surface irradiation cannot have any wavelength which is contained in the measuring light beam. The in particular homogeneous light provided for surface irradiation on the one hand and the measuring light on the other hand can therefore be formed by various wavelengths of light. In this case, the detection system can have at least one wavelength-selective component, particularly a filter. The in particular homogeneous light provided for surface irradiation can in this case be formed by light of a first wavelength range and the measuring light beam can in this case be formed by light of second wavelength range, it being possible for the first wavelength range to be different from the second wavelength range. Thus, a separation of the, in particular homogeneous, light provided for surface irradiation from the measuring light beam can be undertaken by use of filter components arranged downstream, in order to reliably separate the inhomogeneity measurement from the polarization measurement. Thus, a measurement of the liquid sample can be improved.

According to one embodiment of the present invention, the illumination mirror is movable, particularly pivotable, in order to, in the case of various positionings of the illumination mirror (which is movable into these various positionings), alternatively direct either the, in particular homogeneous, light provided for surface irradiation or the measuring light beam onto the sample. Thus, light for inhomogeneity measurement or light for polarization measurement can be provided in a simple manner. In this case, the, in particular homogeneous, light provided for surface irradiation in particular has a wavelength which is equal to a wavelength of the measuring light beam. In particular, the first wavelength range can be equal to the second wavelength range. This embodiment can in particular be advantageous if the light-generating system only contains one light source. This light source can generate light of the first wavelength range which can be equal to the second wavelength range.

According to one embodiment of the present invention, the device further has a polarization state analyzer for changing the polarization state of light which has passed through the sample, whereby the polarization state analyzer can be arranged or is arranged in an analysis beam path upstream of at least a part of the detection system.

The polarization state analyzer can in particular be realized by a polarizer (also termed an analysis polarizer). The analysis polarizer can be used for analyzing the polarization state following the passage of the light through the sample. To this end, the analysis polarizer can in particular be rotatable, in order to allow light, in particular linearly polarized light of various polarization states, to pass through. In particular, the light which has passed through the sample can comprise linearly polarized light, which is linearly polarized along a first direction. The analysis polarizer can be rotated in this manner in order to allow only light of a linear polarization state to pass through, which light is linearly polarized in a second direction. The second direction can in this case in particular be perpendicular to the first direction, in order to achieve a minimization of a light intensity detected by the detection system. The orientation of the analysis polarizer can in this case display the change of the polarization state on the basis of the irradiation through the sample or make the same determinable.

According to one embodiment of the present invention, the detection system has a surface detector in the analysis beam path at least for detecting light, which originates from transmissions through the sample of the in particular homogeneous light provided for surface irradiation. The surface detector can in this case be used for detecting an image of the sample which arises by means of the telecentric imaging of the projection of the sample along the optical axis.

Then, in particular following an analysis of the image, inhomogeneities of the sample can be detected in particular from a detected contrast in the image.

According to one embodiment of the present invention, the surface detector is set up for detecting the measuring light beam transmitted through the sample, particularly if the polarization state analyzer is pivoted into the analysis beam path. Here, the surface detector can be used both for capturing the image for measuring the inhomogeneities of the sample and for carrying out the polarization measurement of the sample. If the surface detector is used for measuring the polarization changing properties of the sample, the telecentric optical system can be pivoted out of or alternatively also stay pivoted into the analysis beam path. Changes of the polarization state of the measuring light beam due to the passage through the lens and/or the further lens, can also be taken into account for determining the polarization changing properties of the sample.

According to one embodiment of the invention, the telecentric optical system can be located in the beam path during the polarization measurement. In this case, the lens(es) for the telecentric optical system can be chosen in such a manner that it (they) does (do) not influence the measurement of the rotation value (for example rotationally symmetrical configuration). If the lens(es) causes (cause) an additional rotation, then this can be corrected or can be taken into account during the determination of the rotation value of the sample. If the aperture diaphragm of the telecentric optical system is too small, it can be opened further during the polarization measurement. An additional photodetector for carrying out the polarization measurement is not required in accordance with this embodiment.

According to one embodiment of the present invention, the surface detector is used both for capturing the image for measuring the inhomogeneities of the sample and for carrying out the polarization measurement of the sample. The telecentric optical system is located in the beam path during the polarization measurement and any polarization changing properties of the telecentric optical system are determined and corrected, if appropriate for each pixel separately. The information for the polarimetric measurement can then be obtained from the two-dimensional image of the surface detector, particularly by integrating across a region of the possibly polarization corrected image.

According to one embodiment of the present invention, as described above, the surface detector is used both for capturing the image for measuring the inhomogeneities of the sample and for carrying out the polarization measurement of the sample. If inhomogeneities, particularly bubbles or particles, are detected in a part region of the two-dimensional image of the surface detector, these regions can be discarded for the polarimetric measurement. In particular, for the polarimetric measurement, integration and/or averaging can be carried out across the regions not affected by inhomogeneities.

According to one embodiment of the present invention, as described above, the polarimetric measurement can be obtained from the two-dimensional image of the surface detector. In this embodiment, one of the arrangements as are known for imaging polarimeters in the prior art can be chosen. In the case of imaging polarimeters, the pixels contain one piece of local polarization information in each case.

According to one embodiment of the present invention, for determining the homogeneous polarization properties of the liquid sample, there is averaged over the spatially resolved polarization information of the two-dimensional image. In particular, regions affected by inhomogeneities can be discarded in this case. (Inhomogeneity can be recognized in the two-dimensional image with spatially resolved polarization information in particular from the polarization contrast exceeding a threshold value). In this case, the spatially resolved polarization information of the two-dimensional image can lead to an improved recognition of inhomogeneities, as the polarization information is particularly sensitive to inhomogeneities.

According to one embodiment of the present invention, the analysis beam path has a first analysis beam path and a second analysis beam path which is different from the first analysis beam path, the detection system having, in the first analysis beam path, the surface detector for detecting light which originates from transmission through the sample of the in particular homogenized or homogeneous light provided for surface irradiation, and having, in the second analysis beam path, a photodetector downstream of the polarization state analyzer for detecting the measuring light beam transmitted through the sample.

The photodetector can in particular have a higher sensitivity than an individual pixel of the surface detector, which can improve a precision or sensitivity of the polarization measurement. Also, the telecentric optical system can just be arranged in the first analysis beam path without being arranged in the second analysis beam path. The telecentric optical system does also not, however, have to be movable or pivotable, but rather can be fixedly installed within the first analysis beam path.

According to one embodiment of the present invention, the device further has a beam splitter which is arranged between the sample and the detection system in order to simultaneously divert a portion of the light transmitted through the sample along the first analysis beam path onto the surface detector and another portion of the light transmitted through the sample along the second analysis beam path onto the photodetector. The beam splitter can in particular allow one portion of light to pass and reflect the other portion of light. The beam splitter can also be constructed as a dichroic beam splitter which, as a function of wavelength, reflects a portion of light and allows another portion of light to be transmitted. Thus, the analysis beam path can reliably be split into the first analysis beam path and the second analysis beam path.

According to one embodiment of the present invention, the device further has a reflector which is arranged between the sample and the detection system such that it can be moved, particularly pivoted in and pivoted out, in order to alternatively (i.e. not simultaneously) divert light transmitted through the sample either along the first analysis beam path onto the surface detector or along the second analysis beam path onto the photodetector. Thus, an inhomogeneity measurement of the sample can be carried out before or following a polarization measurement of the sample.

According to one embodiment of the present invention, the device further has a processing and control system which receives signals from the detection system, based on which the processing and control system determines a two-dimensional image of the irradiated sample (which can represent a projection of the irradiated sample), the processing and control system being constructed in particular to analyze the two-dimensional image by image processing (in particular with respect to a contrast within the image), in order to detect an inhomogeneity, particularly air bubbles and/or streaks, within the sample. The processing and control system can in this case comprise a processor and/or a memory, it being possible to control the processor by way of a program element, by use of which a processing or an analysis of the two-dimensional image is carried out.

Regions of higher or lower intensity in the two-dimensional image can represent air bubbles and/or streaks in particular as surrounding regions of the image.

In particular, the processing and control system can be constructed to investigate the contrast of the two-dimensional image and can for example detect an inhomogeneity if the contrast in the two-dimensional image has exceeded a threshold value.

Furthermore, geometric deviations of the two-dimensional image can be determined from a reference image of a homogeneously filled cuvette. To this end, diverse methods are known in the prior art, which can be applied.

If the two-dimensional image contains spatially resolved polarization information, an inhomogeneity can be detected on the basis of the fact that the polarization contrast exceeds a threshold value.

According to one embodiment of the present invention, the processing and control system is constructed to control the polarization state generator (in the illumination beam path) and/or the polarization state analyzer (in the analysis beam path), so that an orientation of a polarization direction of light, which is allowed through by the polarization state generator and/or the polarization state analyzer, is set, in order to in particular minimize an intensity detected by the detection systems.

In this case, the processing and control system can in particular be constructed to determine from the set orientation, at least one optical property of the sample, particularly a rotation value of a rotation of a polarization direction of the light on the basis of the irradiation of the sample with the measuring radiation and/or a concentration of an optically active component in the sample. Thus a reliable polarization measurement can be carried out.

According to one embodiment of the present invention, the device further has an actuator, particularly an electric motor, in order to pivot the homogenizer and/or the reflector and/or the polarization state analyzer into or out of the optical axis or the analysis beam path. Thus, an inhomogeneity measurement and/or a polarization measurement can alternatively be carried out.

According to one embodiment of the present invention, the device further has a sample holder for holding a sample container, in particular a cuvette for accommodating the sample. In this case, the sample container can be constructed in such a manner that the sample container can be arranged in such a manner relatively to the other components of the optical device that an outlet and an inlet window of the sample container are arranged in the optical axis. The optical device can in particular further have a temperature sensor for measuring the temperature of the sample, it being possible in particular for the temperature sensor to be fixable on the sample container.

In one embodiment of the present invention, the optical device only comprises a single light source and a single surface detector, as well as a telecentric optical system upstream of the surface detector. A homogenizer can be folded into or folded out of the illumination beam path, in order to alternatively direct either homogeneous light or a measuring light beam onto the sample.

In a further embodiment of the present invention, the optical device only comprises a single light source with an inherently homogeneous radiation characteristic and a single surface detector, as well as a telecentric optical system upstream of the surface detector. A separate homogenizer can then be dispensed with.

Generally, alternatively either the measuring beam/polarized beam or the homogenized light for detecting the inhomogeneities can be diverted or mirrored from the optical axis.

DETAILED DESCRIPTION

Figure 1:
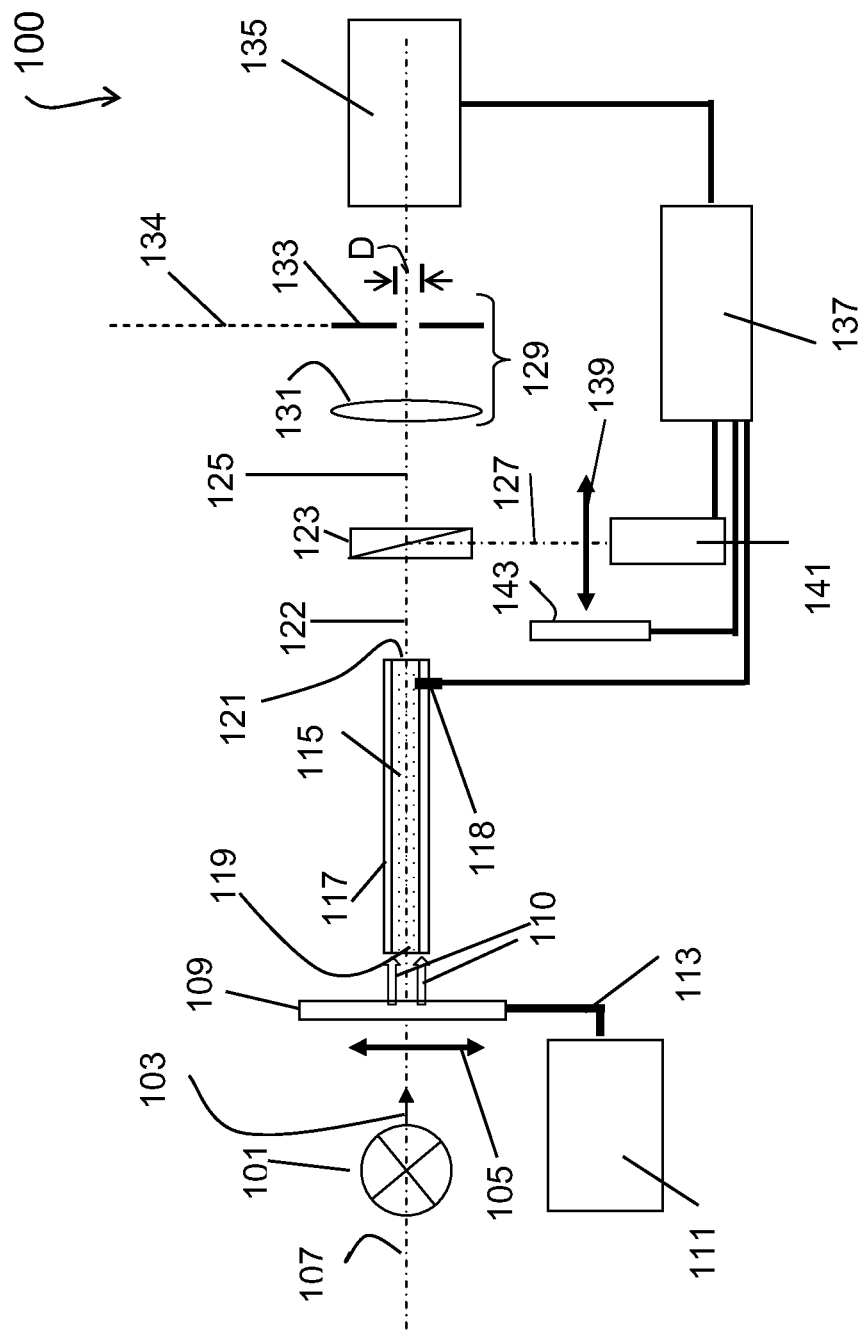
FIG. 1 schematically shows an optical device constructed as a polarimeter according to an embodiment of the present invention.

FIG. 1 schematically shows an optical device 100 according to an embodiment of the present invention, which optical device is constructed as a polarimeter.

The optical device 100 has a light source 101 which represents a light-generating system for generating both homogenized or homogeneous light 110 (i.e. with a lateral intensity distribution) and for generating a measuring light beam 103. The light source 101 to this end comprises a non-illustrated beam-shaping optical system, in order to shape a measuring light beam 103 consisting of parallel light beams. To generate a defined polarization state of the measuring light beam 103, the optical device 100 comprises a polarizer 105, the orientation thereof can be set by means of an actuator which is not illustrated. The measuring light beam 103 which proceeds from left to right along the optical axis 107 in FIG. 1, therefore has a defined polarization state after passage through the polarizer 105.

The optical device 100 further comprises a homogenizer 109 which can be run into or run out of the optical axis 107 by a motor 111 via an arm 113. The homogenizer 109 is used in order to generate light 110 with an even intensity distribution for surface irradiation of the sample 115, which is located in the cuvette 117, from the measuring light beam 103 during passage through the homogenizer 109.

In the event that the polarization-changing properties of the sample 115 should be measured, the homogenizer 109 is removed from the optical axis 107 in order to thus direct the measuring light beam 103, which consists of parallel light beams of a defined polarization state, through an inlet window 119 onto the sample 115 and through the sample 115 and through an outlet window 121.

The optical device 100 comprises a beam splitter 123 downstream of the sample 115, which splits an analysis beam path 122 into a first analysis beam path 125 and a second analysis beam path 127.

In the first analysis beam path 125, a telecentric optical system 129 is arranged with a collimating lens or a lens system 131 and an aperture diaphragm 133 upstream of a surface detector 135. The aperture diaphragm 133 is in this case arranged in the image-side focal plane 134 of the lens or of the lens system 131. The aperture diaphragm 133 has an aperture window of a settable diameter D. In the case of homogeneous illumination of the sample 115, i.e. when the homogenizer 109 is run into the optical axis 107, the sample 115 is illuminated with homogeneous light 110 and a projection of the sample 115 is imaged along the optical axis 107 onto the surface detector 135 in the form of a two-dimensional image by means of the telecentric optical system 129.

Evaluation or investigation is carried out in the two-dimensional image of the projection of the sample 115 with regards to inhomogeneities by use of a control and evaluation component 137. In this case, the presence of bubbles, streaks, foreign bodies, etc. is determined either visually by use of the user or automatically, in particular by use of image recognition software or image processing software. If appropriate, an image of this type can be displayed onto a display unit of the polarimeter or the optical device 100. For a measurement of the homogeneity or inhomogeneity of the sample 115, as detailed above, the homogenizer 109 is arranged in the optical axis (or the illumination beam path) 107.

In order to alternatively, i.e. at another point in time, be able to measure the optical properties or the polarization changing properties of the sample 115, the homogenizer 109 is removed from the illumination beam path 107 by use of the actuator 111, so that the measuring light beam 103 with a defined polarization state consisting of parallel light beams is directed onto the sample 115 and through the same. To this end, the portion of light which has been diverted along the second illumination beam path 127 by the beam splitter 123 is further evaluated. This portion of the light in the second analysis beam path 127 falls through an analysis polarizer 139 and is detected by means of a photodetector 141 with regards to the intensity of the light which is let through.

Further components of a typical polarimeter, such as for example windows, apertures, Faraday polarizers, Glan-Thompson polarizers etc. are not shown here for the sake of clarity.

Electrical signals which correspond to the intensity of the registered light are also guided to the control and evaluation unit 137. The analysis polarizer 139 can be rotated by a motor 143 in accordance with corresponding control signals of the control and processing module 137, in order to minimize an intensity of light which is registered by the photodetector 141. The angle (rotation value), through which the polarization direction of the measuring light beam 103 has been rotated on account of the passage through the sample 115, can then be determined from the orientation of the set analysis polarizer 139. A property of the sample, such as for example a concentration of at least one optically active component, can in turn be determined from this rotation value by the control and processing system 137.

In a further embodiment of the present invention, the surface detector 135 can be used both for the polarization measurement as well as for detecting inhomogeneities. An additional photodetector 141 is not necessary in such a case. For this combined use of the surface detector 135, the analysis polarizer 139 is arranged in the second analysis beam path 125 either upstream of the telecentric optical system 129 or downstream of the telecentric optical system 129.

The aperture diaphragm 133, also denoted telecentric diaphragm 133, can be realized as a transmissive LCD element fixedly mounted in the focal plane 134 of the lens 131, which reversibly optionally allow the entire beam cross section of the measuring radiation 103 for the polarimetric measurement to pass or in the reversed state only allows a small central region of the beam to pass, in order to thus act as a telecentric diaphragm. The LCD element can be realized in such a manner that a plurality of diameters of the diaphragm opening (diameter D in FIG. 1) can be set, so that depending on the light attenuation due to an if necessary strongly absorbing sample, an optimum ratio of light intensity on the one hand and telecentric action as well as depth of focus on the other hand can be set.

In a further embodiment, the aperture diaphragm 133 can have an iris diaphragm as telecentric diaphragm which can be varied in terms of diameter D. The telecentric diaphragm 133 can thus be realized as an element which can be changed mechanically in terms of its size, it being possible to vary the size of the aperture window, for example mechanically, such as for example by use of an iris diaphragm.

A temperature sensor 118 transmits data, which display the temperature, to the control and processing system 137.

Figure 2:
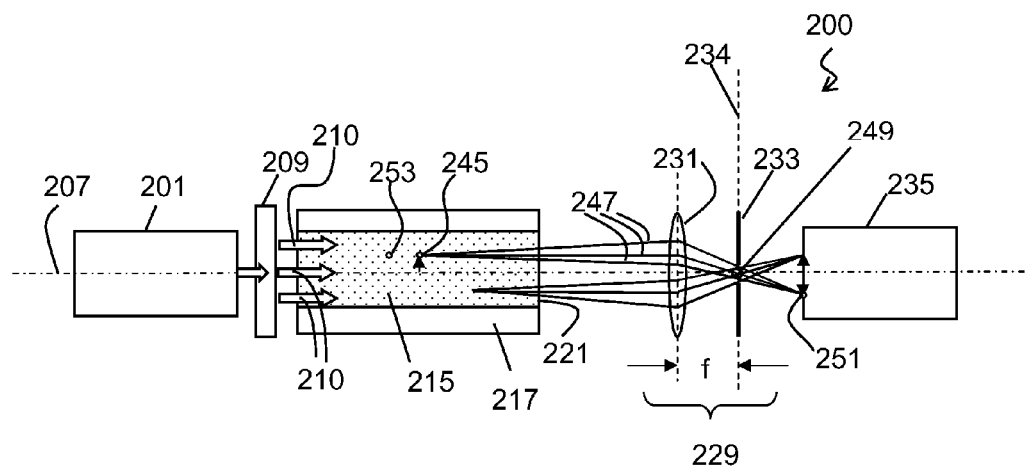
FIG. 2 schematically shows an object-side telecentric optical system, as it is used in the polarimeter of FIG. 1.

FIG. 2 schematically shows an embodiment of an object-side telecentric optical system 200, as it is used in the polarimeter of FIG. 1. More specifically, FIG. 2 shows details of the telecentric imaging as it is used in the polarimeter 100 of FIG. 1. The telecentric imaging of the telecentric optical system 229 forms the projection of the sample 215 along the optical axis 207 onto pixel elements of the surface detector 235 arranged at a surface. To this end, the sample 215 is surface illuminated with homogenized light 210 by means of a light source 201 and a homogenizer 209. The homogenized light 210 enters the cuvette 217 at a first window and exits the cuvette 217 at outlet window 221.

Light beams 247 emanate from a point 245 of the sample 215 and are refracted by means of the lens 231 of the telecentric optical system 229 towards the focal point in the focal plane 234. The focal point is in this case designated by the reference number 249. The aperture diaphragm 233 is arranged in the image-side focal plane of the lens 231, which has the focal length f, as is illustrated in FIG. 2. The object point 245 is therefore imaged onto the pixel 251, as is registered by the surface detector 235. Another object point 253, which is just as far from the optical axis 207 and is remote in the same direction as the object point 245, is likewise imaged with the same imaging scale onto the image point 251, onto which the object point 245 is also imaged. The pixel 251 therefore contains information about a projection of the sample 215 along the optical axis 207. If further object points of the sample 215 are considered, which are arranged along various directions and at various distances from the optical axis 207, then a two-dimensional image results on the surface detector 235, which constitutes a projection of the sample 215 along the optical axis 207.

Figure 3:
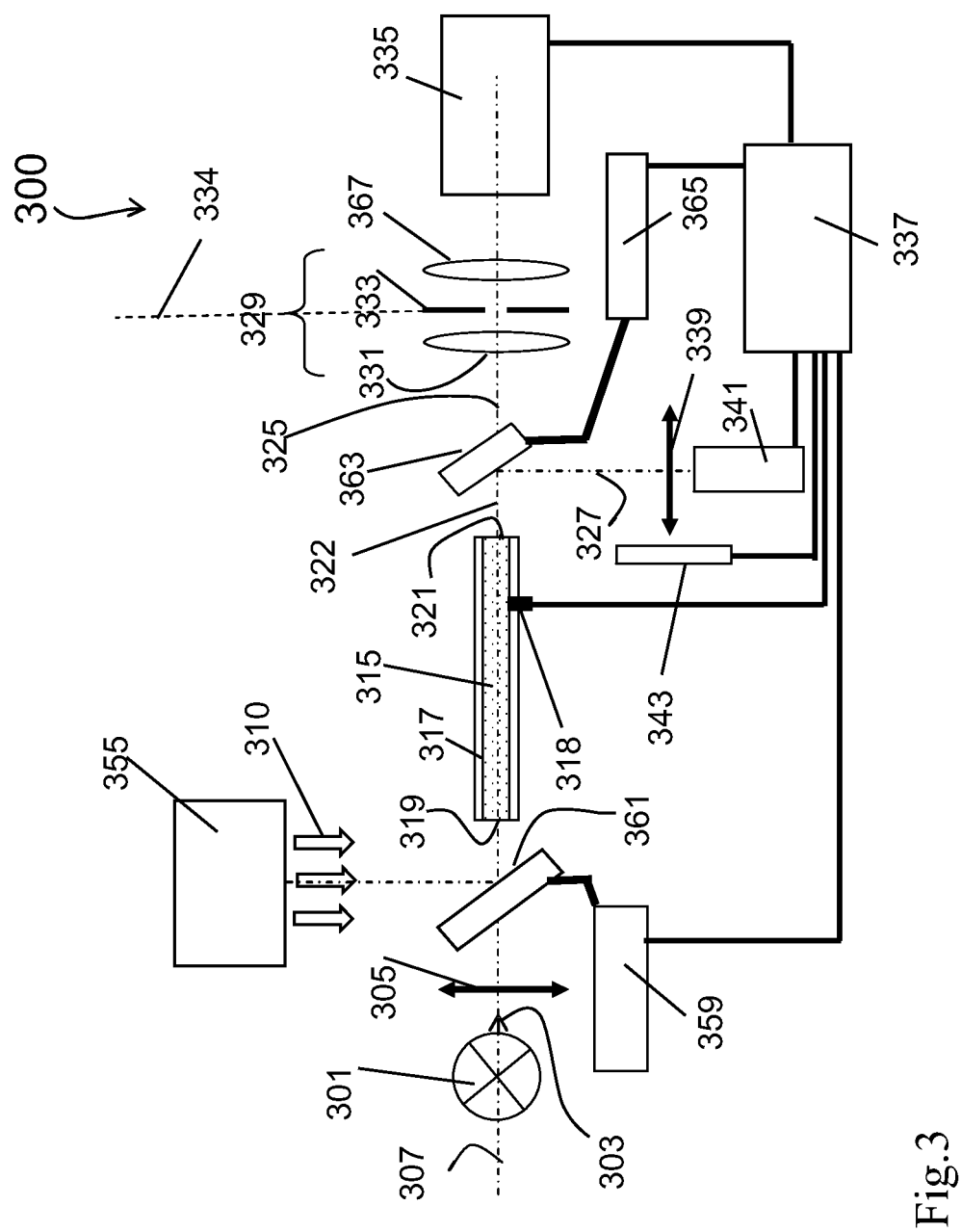
FIG. 3 schematically shows an optical device, particularly a polarimeter, according to a further embodiment of the present invention.

FIG. 3 schematically illustrates an optical device 300 according to a further embodiment of the present invention. In contrast to the optical device 100, which is illustrated in FIG. 1, the optical device 300 in FIG. 3 has a double telecentric optical system 329 which is both object-side telecentric and image-side telecentric. Other components of the optical device 300 are similar to optical components of the optical device 100 in terms of structure and/or function and are provided with reference numbers which only differ in terms of the first digit. A corresponding detailed description of some of these components can therefore be drawn from the description of FIG. 1 or 2.

In addition to the light source 301, which also has the optical device 100 in FIG. 1, the optical device 300 further comprises a further homogenized or homogeneous light source 355 which generates and emits homogeneous light 310. For illuminating the sample 315 with the homogenized or homogeneous light 310, the reflector (in the following also termed mirror) 361 is introduced into the illumination beam path 307 by the actuator 359, the homogenized or homogeneous light 310 being reflected at the mirror 361 in order to pass through the inlet window 319 of the cuvette, through the sample 315 and to exit the cuvette 317 through the outlet window 321.

In order to assess or to measure the homogeneity of the sample 315, a mirror 363 is removed from the analysis beam path 322 by operation of the actuator 365, so that following transmission through the sample 315 the homogenized or homogeneous light 310 falls onto the double telecentric optical system 329.

The double telecentric optical system 329 comprises the lens (or lens system) 331, the aperture diaphragm 333 and a further lens (or lens system) 367, the further lens 367 being arranged in such a manner that the aperture diaphragm 333 is arranged in the object-side focal plane 334 of the further lens 367. Further, the aperture diaphragm 333 is arranged (as in the device 100 of FIG. 1) in the image-side focal plane 334 of the lens 331.

Figure 4:
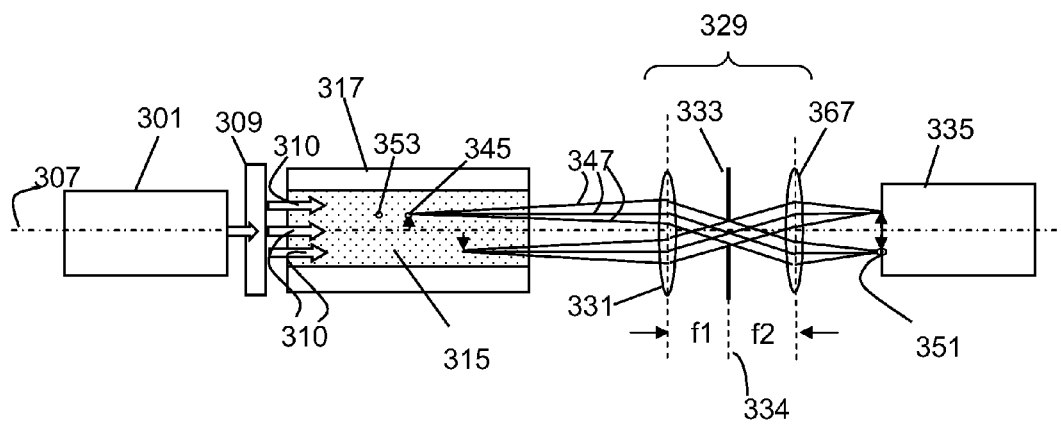
FIG. 4 schematically shows an object-side and image-side telecentric optical system, as it is used in the polarimeter of FIG. 3.

Thus, object points 345, 353 with the same distance to the optical axis 307 are imaged onto one and the same pixel 351 of the surface detector 335 independently of the position thereof along the optical axis 307, as can be seen from FIG. 4 which illustrates double telecentric imaging.

The surface detector 335 therefore registers a two-dimensional image which represents a projection of the sample 315 along the optical axis 307 and forwards corresponding electrical signals to the control and processing system 337.

In one embodiment, the two-dimensional image is presented and it is left to the user to assess the filling quality. In a further embodiment, the control and processing system 337 can determine a degree of the homogeneity or a degree of the inhomogeneity of the sample 315 from the image data in that the two-dimensional image is analyzed with regards to the contrast thereof. The determination of the contrast in this case comprises the determination of minimum intensity values and maximum intensity values or a variance of the intensity values of the two-dimensional image. If, for example, the variance of the intensity values within the two-dimensional image exceeds a certain limit, then an inhomogeneity within the sample, for example due to air bubbles or streaks, can be deduced, which may cause a polarization measurement of the sample to appear inaccurate. To this end, measures can be taken, such as shaking the sample, removing the bubbles, etc., in order to reduce or eliminate the inhomogeneities within the sample which have been detected.

When reflector 363 is not present in the analysis beam path 322, the homogenous light 310 is reflected by mirror 361 and following transmission through the sample 315 the homogenized or homogeneous light 310 represented by optical path 325 falls onto the double telecentric optical system 329. Following a renewed inhomogeneity measurement, it can be determined that the homogeneity is then sufficient in order to then be able to carry out a reliable polarization measurement. To this end, the mirror 363 is run into the analysis beam path 322 and the mirror 361 is removed from the illumination beam path 307, in order to thereby allow measuring radiation 303, which has a defined polarization state due to the polarizer 305, to pass onto the sample 315 and through the same. Following reflection at the reflector 363 run into the analysis beam path 322, the reflected measuring light radiation follows optical path 327 and passes through the analysis polarizer 339 and then falls into the photodiode or photodetector 341, in order to generate electrical signals corresponding to the intensity. In turn, the analysis polarizer 339 can be changed in terms of the orientation thereof by means of a motor 343 which is controlled by the control and processing system 337.

FIG. 4 again shows a section of the optical device 300 of FIG. 3, only the telecentric optical system 329 being illustrated in enlarged detail, in order to clarify the mode of action thereof. To this end, the sample 315 is surface illuminated with homogenized light 310 by means of a light source 301 and a homogenizer 309. Light beams 347 emanate from a point 345 of the sample 315 and are refracted by means of the lens 331 of the telecentric optical system 329 towards and beyond the aperture diaphragm 333 on their way to lens 367, where the light beams 347 are further refracted. The lens 331 is arranged upstream of the aperture diaphragm 333 at a distance f1, the distance f1 corresponding to the focal length of the lens 331. Further, the further lens 367 is arranged downstream of the aperture diaphragm 333 at a distance f2, the distance f2 corresponding to the focal length of the further lens 367. The object points 345, 353, which have the same distance to the optical axis 307 and are spaced away from the optical axis 307 in the same direction, are imaged onto the pixel 351 independently of their position along the optical axis 307, the incoming intensity of light at this point 351 being detected in a spatially resolved manner by the surface detector 335.

A beam path which is telecentric on both sides is the combination of an object-side and image-side telecentric beam path. An image-side telecentric beam path arises in the simplest case by means of an aperture diaphragm in the object-side focal plane of a collimating lens.

Entrance and exit pupils are located at infinity, consequently the system is afocal. In contrast with the purely object-side telecentry, the tolerable object position is here not limited by the depth of focus. One can refocus the image plane without changing the imaging scale. The simplest structure to this end consists of the two collimating lenses 331 and 367, between which the aperture diaphragm 333 is arranged. The distance of a lens from the aperture diaphragm must correspond to the respective focal length f1 or f2.

The simply telecentric system 100 (FIGS. 1, 2) stands out by means of a more cost-effective design (only one lens 131, a more simple barrel system). A shorter overall length also results therefrom.

The imaging quality—and as a result the resolution—is limited by the size of the telecentric diaphragm 133, 333 and becomes lower, the smaller the diaphragm is. At the same time, the depth of focus range also becomes larger however, the smaller this diaphragm is. The choice of the optimum diaphragms 133, 333 and lens dimensions (133, 333, 367) is therefore determined by the maximum cuvette dimensions which should be imaged. Typical diaphragm diameters here lie in the range of some or several hundred micrometers.

The light sources 301 and 355 in FIG. 3 can in this case in particular generate light of separated wavelength ranges and if the reflector 361 and reflector 363 are respectively realized as a partially transparent reflector, a measurement of the polarization properties and the homogeneity of the sample 315 can take place simultaneously. Here, for example, the splitting of the components can also take place with a Faraday polarizer in different frequency ranges if the light used for polarization measurement is (periodically) modulated by use of the Faraday polarizer and thus can be detected separately.

The invention claimed is:

1. An optical device for analyzing a liquid sample, comprising:
    a light-generating system for generating light for surface irradiation of the sample through an inlet window of a cuvette, wherein the inlet window traverses a longitudinal axis of the cuvette;
    a detection system arranged to intercept the surface irradiation after passage through the sample;
    a telecentric optical system with a lens arranged between the sample and the detection system and with an aperture diaphragm in a focal plane of the lens between the lens and the detection system.

2. The device according to claim 1, wherein the telecentric optical system has a further lens arranged between the aperture diaphragm and at least one part of the detection system.

3. The device according to claim 1, further comprising an actuator that positions at least one of a homogenizer, a reflector, and a polarization state analyzer into an optical axis or an analysis beam path.

4. The device according to claim 1, further comprising a temperature sensor for measuring a temperature of the sample.

5. The device according to claim 1, further comprising a processing and control system which receives signals from the detection system, based on which the processing and control system determines a two-dimensional image of the irradiated sample, which represents an optical projection of the sample along an optical axis, wherein the processing and control system is configured to display and/or store and/or analyze the two-dimensional image by use of image processing, to detect an inhomogeneity within the sample.

6. The device according to claim 1, further comprising a polarization state analyzer for changing a polarization state of light which has passed through the sample, wherein the polarization state analyzer is arranged in an analysis beam path upstream of at least a part of the detection system.

7. The device according to claim 1, wherein the light-generating system is further configured for generating a measuring light beam, which propagates through the sample along an optical axis.

8. The device according to claim 5, wherein the processing and control system is constructed to control a polarization state generator and/or a polarization state analyzer, so that an orientation of a polarization direction of light, which is let through by the polarization state generator and/or the polarization state analyzer, is set to minimize an intensity detected by the detection system,
    wherein the processing and control system is configured to determine from the set orientation a rotation value of a rotation of a polarization direction of the light based on irradiation of the sample with a measuring radiation and/or a concentration of an optically active component in the sample.

9. The device according to claim 6, wherein the detection system comprises a surface detector in the analysis beam path.

10. The device according to claim 9, wherein the surface detector is configured for detecting the measuring light beam transmitted through the sample when the polarization state analyzer is pivoted into the analysis beam path.

11. The device according to claim 9,
    wherein the analysis beam path comprises a first analysis beam path and a second analysis beam path which is different from the first analysis beam path,
    wherein the detection system comprises, in the first analysis beam path, the surface detector for detecting light which originates from transmission through the sample and, in the second analysis beam path, a photodetector arranged downstream of the polarization state analyzer for detecting the measuring light beam transmitted through the sample.

12. The device according to claim 11, further comprising a beam splitter which is arranged between the sample and the detection system and is set up to simultaneously direct a portion of the light transmitted through the sample along the first analysis beam path onto the surface detector and another portion of the light transmitted through the sample along the second analysis beam path onto the photodetector.

13. The device according to claim 11, further comprising a reflector which is arranged between the sample and the detection system such that it can be pivoted in and pivoted out, in order to alternatively direct light transmitted through the sample along the first analysis beam path either onto the surface detector or along the second analysis beam path onto the photodetector.

14. The device according to claim 7, further comprising a polarization state generator which is arranged upstream of the sample in the optical axis and is configured to generate the measuring light beam with a defined polarization state together with the light generating system.

15. The device according to claim 7, further comprising a homogenizer which is arrangeable in the optical axis.

16. The device according to claim 7, wherein the light-generating system comprises a first light source for generating the surface irradiation and a second light source for generating the measuring light beam, wherein the device further comprises an illumination mirror that directs one of homogeneous light and/or the measuring light beam through the sample.

17. The device according to claim 15, wherein the homogenizer is pivotable out of the optical axis and into the optical axis, to alternatively direct one of a measuring light beam or a homogenized surface irradiation through the sample.

18. The device according to claim 16, wherein the illumination mirror is partially transparent to simultaneously direct both the homogeneous light and the measuring light beam through the sample, wherein the homogeneous light provided for surface irradiation does not comprise any wavelength which is contained in the measuring light beam, and wherein the detection system further comprises a wavelength-selective component.

19. The device according to claim 16, wherein the illumination mirror is movable to various positions to alternatively direct one of the homogeneous light or the measuring light beam through the sample, wherein the homogeneous light provided for surface irradiation comprises a wavelength which is equal to a wavelength of the measuring light beam.

* * * * *